United States Patent [19]

Wright, Jr. et al.

[11] Patent Number: 5,708,507
[45] Date of Patent: Jan. 13, 1998

[54] TEMPERATURE RESOLVED MOLECULAR EMISSION SPECTROSCOPY OF MATERIALS

[75] Inventors: Robert L. Wright, Jr., Dayton; Costandy S. Saba, Springfield; David W. Johnson, Yellow Springs; James D. Wolf, Kettering, all of Ohio

[73] Assignee: The United States of America as represented by the Secretary of the Air Force, Washington, D.C.

[21] Appl. No.: 632,210

[22] Filed: Apr. 15, 1996

[51] Int. Cl.$^6$ .................... G01N 21/72; G01N 21/74
[52] U.S. Cl. .................... 356/417; 356/315; 356/312
[58] Field of Search .................... 356/312, 315, 356/417

[56] References Cited

U.S. PATENT DOCUMENTS

| | | | |
|---|---|---|---|
| 3,824,016 | 7/1974 | Woodriff et al. | 356/312 |
| 3,843,257 | 10/1974 | Wooten | 356/36 X |
| 4,035,079 | 7/1977 | Sperling | 356/312 |
| 4,204,770 | 5/1980 | Tomoff | 356/312 |
| 5,066,125 | 11/1991 | Rogers et al. | 356/312 X |

OTHER PUBLICATIONS

Belcher et al; "Molecular Emission Cavity Analysis—A New Flame Analytical Technique Part I Description of the Technique and the Development of a Method for the Determination of Sulfur"; Analytica Chemica Acta 67(1973) 1-16.

Schubert et al "Determination of Sulfite and Sulfate in Solids by Time-Resolved Molecular Emission Spectrometry" Analytical Chemistry; vol. 51 8 Jul. 1979; pp. 1297-1301.

*Primary Examiner*—Vincent P. McGraw
*Attorney, Agent, or Firm*—Bobby D. Scearce; Thomas L. Kundert

[57] ABSTRACT

System and method for temperature resolved molecular emission spectroscopy of solid, liquid or gaseous materials are described wherein a sample is vaporized and decomposed, and the vaporous sample is transported into a combustion flame; a spectrum of intensity of the optical emission from the flame at a selected wavelength versus temperature of the sample define molecular peaks which are characteristic of the sample material and allows both qualitative and quantitative analysis of the sample.

17 Claims, 4 Drawing Sheets

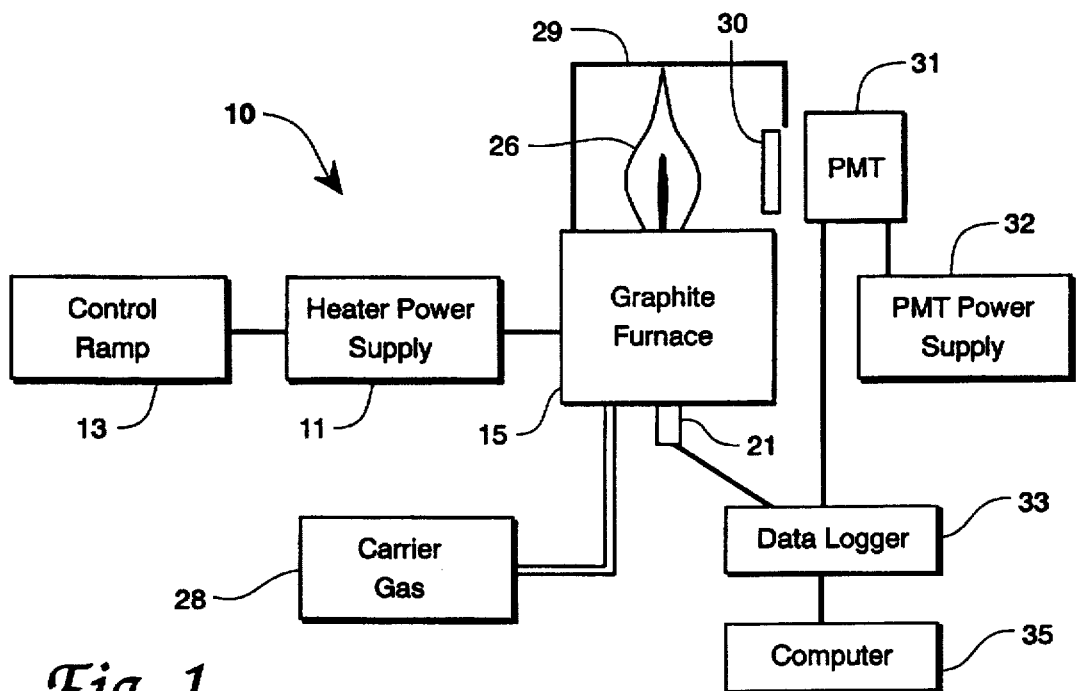
*Fig. 1*
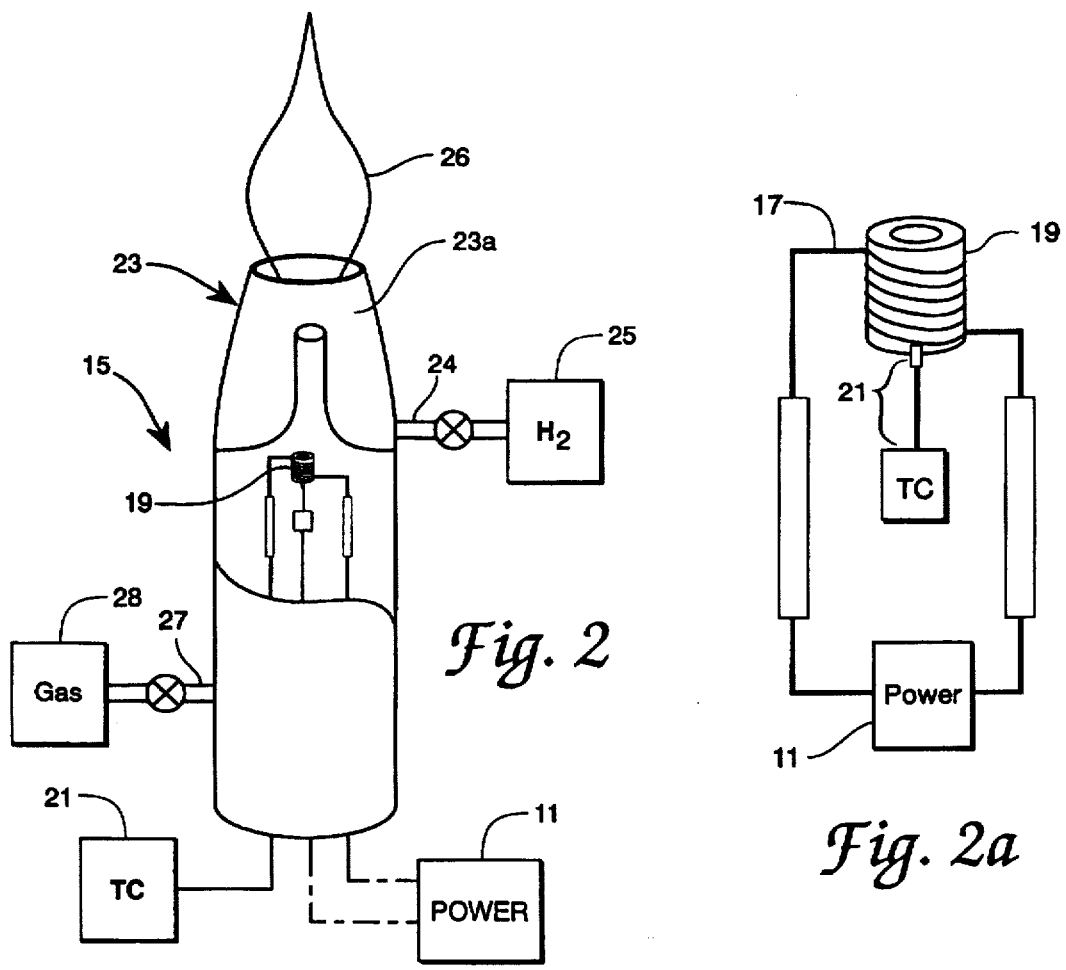
*Fig. 2*  *Fig. 2a*

TEMPERATURE RESOLVED MOLECULAR EMISSION SPECTROSCOPY OF MATERIALS

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems and methods for quantitative chemical analysis utilizing emission spectroscopy, and more particularly to an analytical system and method for temperature resolved molecular emission spectroscopy of materials.

The invention comprises system and method for temperature resolved molecular emission spectroscopy of solid materials wherein samples are thermally decomposed and vaporized in a graphite crucible. The sample vapors are transported by a carrier gas into a cool combustion flame. The optical radiation from the flame is passed through an interference filter and focused onto an optical detector. Data defining the optical emission from the flame as a function of crucible temperature provides a determination of any chemical species for which molecular emission bands are known. Temperatures at which peaks are detected in the spectra are characteristic of the molecular state in which the species existed within the sample, while the area under the peak is proportional to the quantity present. Through appropriate temperature control, different chemical forms of the element species can be determined simultaneously, and both the quantity and nature of the decomposed species can be determined. Reproducibility of the decomposition temperature is typically ±2% with detectability below one ppm. The method of the invention is applicable to a wide variety of materials, and may be applied to gaseous or liquid as well as solid samples, but is particularly useful for the determination of sulfur, phosphorus or nitrogen containing compounds identified as candidate high temperature lubricant materials.

It is therefore a principal object of the invention to provide novel spectral analysis system and method for solid, liquid or gaseous materials.

It is another object of the invention to provide system and method for temperature resolved molecular emission spectroscopy of solid materials.

It is a further object of the invention to provide system and method for temperature resolved molecular emission spectroscopy of sulfur, phosphorus or nitrogen containing materials These and other objects of the invention will become apparent as the detailed description of representative embodiments proceeds.

SUMMARY OF THE INVENTION

In accordance with the foregoing principles and objects of the invention, system and method for temperature resolved molecular emission spectroscopy of solid, liquid or gaseous materials are described wherein a sample is vaporized and decomposed, and the vaporous sample is transported into a combustion flame; a spectrum of intensity of the optical emission from the flame at a selected wavelength venus temperature of the sample define molecular peaks which are characteristic of the sample material and allows both qualitative and quantitative analysis of the sample.

BRIEF DESCRIPTION OF THE DRAWINGS

The invention will be more clearly understood from the following detailed description of representative embodiments thereof read in conjunction with the accompanying drawings wherein:

FIG. 1 is a schematic block diagram of the essential components of the temperature resolved molecular emission spectrometer representative of the invention;

FIGS. 2 and 2a show schematic structural details of the sample container and combustion flame support structure for the FIG. 1 spectrometer system;

DETAILED DESCRIPTION

Figure 3:
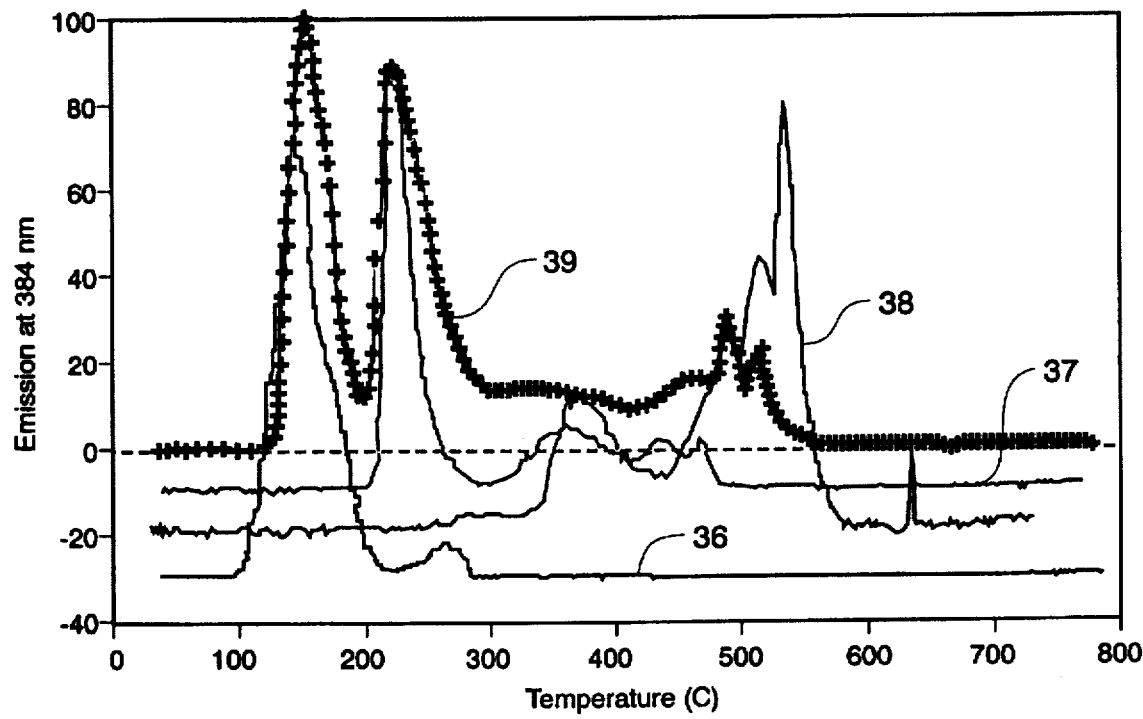
FIG. 3 shows temperature resolved emission traces defined on a plot of relative optical emission of a sample at 384 nm versus temperature, generated utilizing the FIG. 1 system, for the identification of sulfur in a mixture of elemental sulfur, cesium oxythiotungstate and tungsten disulfide and for each of the individual components of the mixture.

Referring now to the drawings, FIG. 1 shows a schematic block diagram of the essential components of a temperature resolved molecular emission spectrometer system 10 representative of the invention. FIGS. 2 and 2a show schematic structural details of the sample container and combustion flame support torch structure for representative system 10.

In system 10, a source of power including power supply 11 operable in a constant current mode and control ramp 13 is operably connected to graphite furnace 15 for controllably heating a sample contained therein. In system 10 built in demonstration of the invention, power supply 11 was capable of delivering 50 amps at 25 V. Power supply 11 was configured to have a current limit corresponding to a maximum temperature within furnace 15 of 1600° C. Referring now additionally to FIGS. 2 and 2a, furnace 15 of demonstration system 10 comprised a tungsten wire 17 wound graphite crucible 19 for containing a sample for analysis. In the demonstration system 10, crucible 19 was configured to have a sample capacity of about 10–20 mg. Thermocouple 21 (tungsten-tungsten 26% rhenium) disposed within a small cavity in crucible 19 provided means for monitoring temperature of the sample. Torch structure 23 having inlet 24 for flowing hydrogen from source 25 was disposed atop crucible 19 for supporting a hydrogen flame 26 in the practice of the invention. Inlet 27 in torch structure 23 was connected to source 28 of a suitable carrier gas, such as argon, helium, nitrogen or mixtures with reactive gases such as air (i.e., oxygen or other gas depending on the sample material), for providing a purging flow of gas at preselected flow rate past crucible 19 and into the center of flame 26. In the structure of demonstration system 10, crucible 19 was configured to be removable from torch structure 23 in order to facilitate insertion and removal of samples without moving torch structure 23 relative to the detector. Light shield 29 was disposed around flame 26, filter 30 and detector 31 as suggested in FIG. 1 in order to exclude extraneous ambient light from measurements made in the practice of the invention, and was silvered on the inner surface in order to maximize the amount of light from flame 26 which is collected by detector 31.

In a preferred embodiment of the invention, flame 26 is a hydrogen-argon entrained air diffusion flame which produces temperatures of less than 1000° C. Other combustion gases and gas mixtures which may be used in contemplation of the invention to support a flame on torch 23 include hydrogen-air or others as would occur to the skilled artisan practicing the invention. A small oxygen flow from a source (not shown) may be added to the combustion gas in order to promote combustion within flame 26. The upper portion 23a of torch structure 23 may be configured as a mixing chamber for the carrier gas and combustion gas flowing therethrough. The temperature of flame 26 is maintained at a relatively low temperature (viz., about 1000° to 1100° C.) in order to maximize formation of the simple molecular species. Higher temperatures result in formation of mainly atomic species. An argon flow rate of about one liter per minute provided maximum sensitivity for sulfur. The tapered shape for torch structure 23 near flame 26 concentrates all of the emission in a narrow band in the central core of the flame.

Interference filter 30 is disposed between flame 26 and a detector, preferably in the form of photomultiplier tube 31, for detection and analysis of the radiation emitted from flame 26. Other detector types may be used in the practice of the invention, as would occur to the skilled artisan, including avalanche diode detectors, photodiode detectors, diode array detectors, or the like. Selection of filter 30 depends on the specific material being detected, the criterion for filter selection may be summarized as follows: that the filter shall pass wavelength bands appropriate to the characteristic emissions of the species analyzed for. Accordingly, filter 30 for use in the detection of sulfur in flame 26 is preferably configured for 380 nm with 10 nm bandpass; for phosphorus, a 530 nm filter with a 10 nm bandpass is desired. Filters for detection of other elements may include 520 nm for detection of nitrogen containing species and 360 nm, 370 nm and 410 nm for detection of chlorine, bromine and iodine containing species, as would occur to the skilled artisan guided by these teachings. In system 10, photomultiplier tube 31 was operatively connected to a 1200V variable power supply allowing controllable sensitivity of the detector.

In practice of the invention, graphite crucible 19 is withdrawn from torch 23 assembly, and a sample for testing is introduced into crucible 19 and torch 23 is reassembled. Combustion flame 26 is then established atop torch structure 23 and flow of carrier gas past crucible 19 from inlet 27 is initiated. Furnace 15 is heated to selected temperature (normally a maximum of about 1200° C.) by suitable control of current from power supply 11. The optical molecular emission from flame 26 as detected at 31 and the corresponding temperature of crucible 19 as read by thermocouple 21 are measured at selected time intervals (such as one second) until the sample has been completely vaporized or decomposed. A sample (crucible 19) temperature of less than 1200° C. is preferable because at temperatures above this black body radiation from graphite crucible 19 begins to interfere with the measurement of the molecular emission from flame 26. Data representing the molecular emission and temperature measurements may be collected and stored using any suitable means such as that depicted in FIG. 1 as data logger 33 and computer 35.

Figure 4:
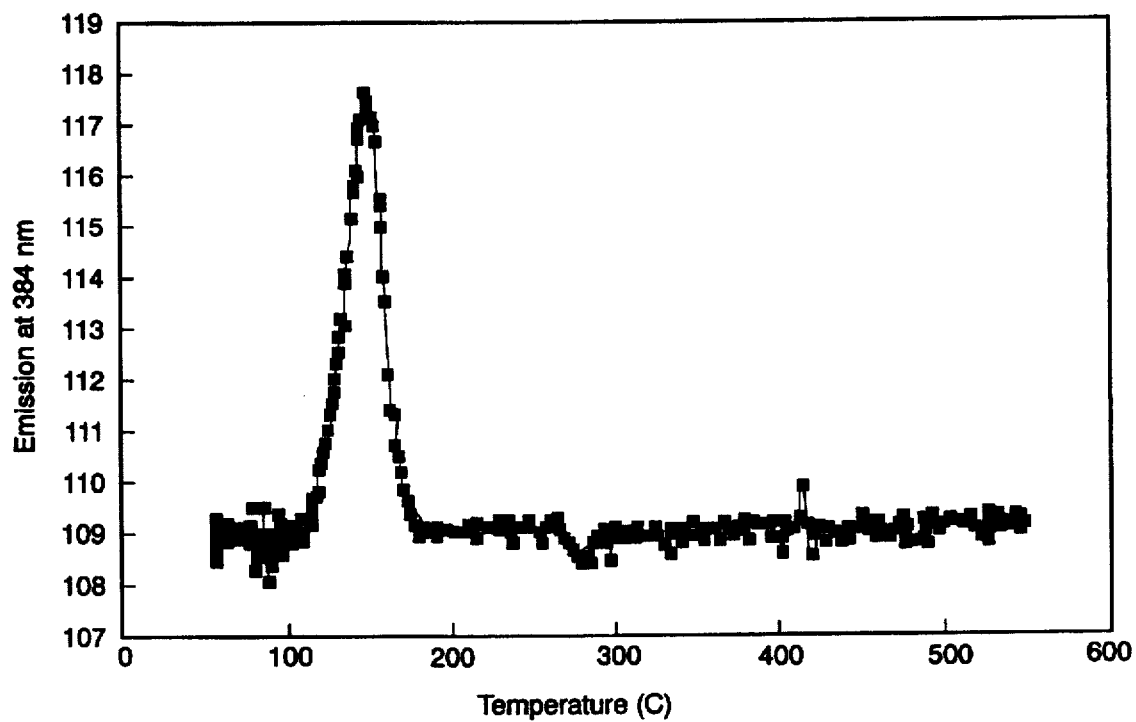
FIG. 4 shows temperature resolved molecular emission trace for a 100 ng sample of elemental sulfur obtained using the FIG. 1 system.

Referring now to FIG. 3, shown therein are temperature resolved emission traces defined on a plot of relative optical emission of a sample at 384 nm versus temperature, generated utilizing demonstration system 10, for the identification of sulfur in a mixture of elemental sulfur, cesium oxythiotungstate and tungsten disulfide and for each of the individual components of the mixture. Trace 36 corresponds to a sample of elemental sulfur, trace 37 to cesium oxythiotungstate, trace 38 to tungsten disulfide, and trace 39 to the mixture. The average temperatures at which the major emissions were observed in the mixture for sulfur was 150.3° C. (average of 10 runs, standard deviation (s.d.) 9.1° C.), for tungsten disulfide 222.0° C. (average of 9 runs, s.d. 11.4° C.), and for cesium oxythiotungstate 477.8° C. (average of 10 runs, s.d. 13.3° C.). All materials used in demonstration of the invention were of, at least, reagent grade purity. FIG. 4 shows a further trace for a sample containing 100 ng of elemental sulfur. The detection limit for sulfur (sulfur mass required to produce a peak twice the s.d. of the baseline) was found to be 50 ng and 200 ng for elemental sulfur and sulfur in cesium oxythiotungstate, respectively.

Figure 5:
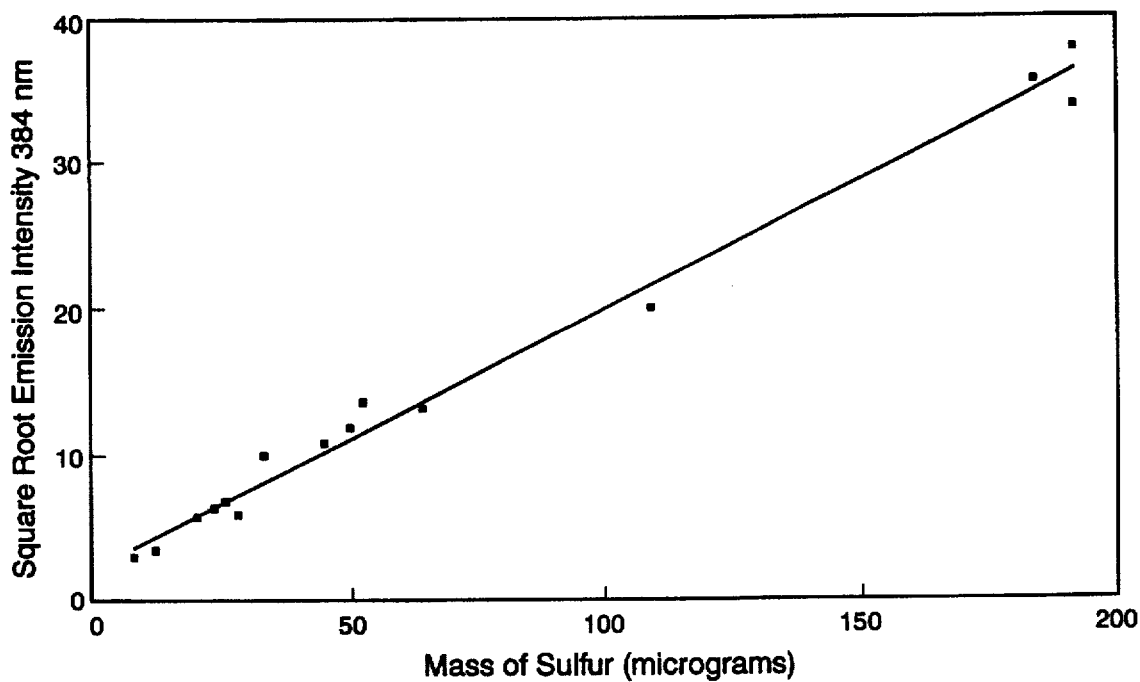
FIG. 5 shows a calibration curve defined on a plot of the square root of emission intensity at 384 nm versus sulfur mass for determination of sulfur by molecular emission using the FIG. 1 system.
Figure 6:
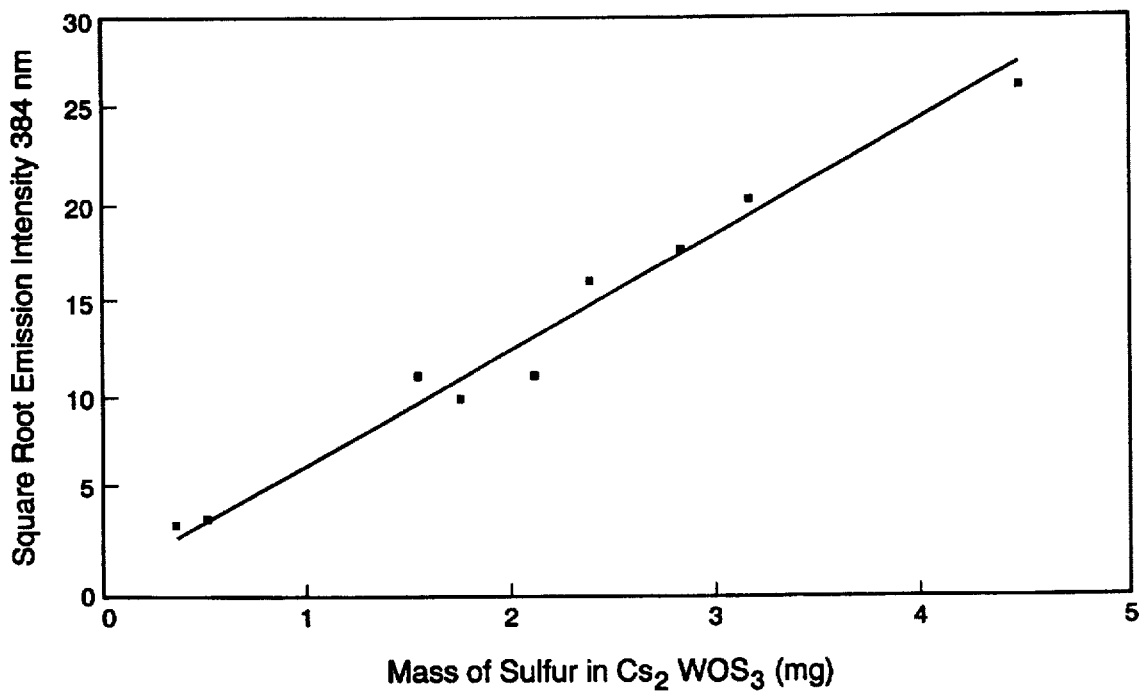
FIG. 6 shows a calibration curve defined on a plot of the square root of emission intensity at 384 nm verus sulfur mass for the determination of sulfur in cesium oxythiotungstate by molecular emission of sulfur using the FIG. 1 system.

Referring now to FIGS. 5 and 6, shown therein, respectively, are calibration curves defined on plots of the square root of emission intensity at 384 nm versus sulfur mass for the determination of sulfur and for the determination of sulfur in cesium oxythiotungstate by molecular emission of sulfur using the FIG. 1 system. The curves are substantially linear over the entire range of sulfur mass, but with substantially different slopes which may be due to the greater width of the emission versus temperature curve and the higher decomposition temperature observed for cesium oxythiotungstate.

Figure 7:
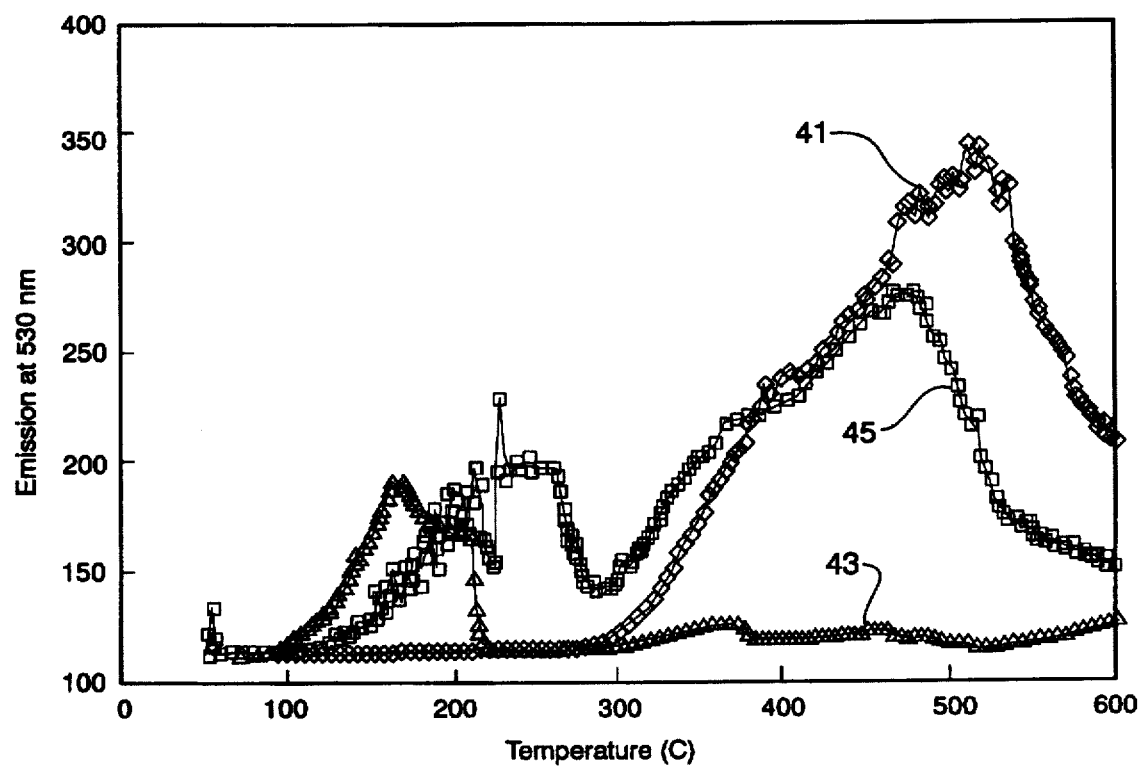
FIG. 7 shows temperature resolved molecular emission spectra obtained using the FIG. 1 system for phosphoric acid, tricresylphosphate and a mixture of the two.

Tests in demonstration of the invention show that phosphorus, determined as the HPO molecule, can also be determined by temperature resolved molecular emission spectroscopy. Referring now to FIG. 7, shown therein are temperature resolved molecular emission spectra obtained using the FIG. 1 system for phosphoric acid (plot 41), tricresylphosphate (plot 43), and a mixture of the two (plot 45). Decomposition temperatures for phosphoric acid, tricresylphosphate and triphenyl phosphine have been shown to be substantially different. The temperature resolution is adequate to identify the three components in the mixture. The maximum temperature practical in the determination of phosphorus is slightly lower than for the determination of sulfur due to the larger fraction of the black body radiation which is emitted within the wavelength range transmitted by the interference filter (530 nm). The determination of phosphorus by molecular emission is interfered with by the molecular emission of the NO molecule, and samples for the quantitative determination of phosphorus should therefore not have nitrogen containing contaminants.

Nitrogen can be determined using the invention at 530 nm, at which wavelength NO is the emitting species. A sample of potassium nitrate decomposes to give a nitrogen emission at a temperature of 450° C. Other materials may be detected in the system of the invention by utilizing the appropriate chemical reaction within crucible 19 and flame 26. For example, determination of the halogens may be accomplished by addition of indium to crucible 19 to form the volatile InX molecules (X is Cl, Br or I). Any species which can be generated by the addition of reagents to the sample cup can be determined using this instrument.

The invention therefore provides an analytical system and method for temperature resolved molecular emission spectroscopy of materials. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

We claim:

1. A temperature resolved molecular emission spectrometer system, comprising:
   (a) a controllably heated crucible for vaporizing a sample material for analysis;
   (b) means for measuring the temperature of said heated crucible;
   (c) means for supporting a combustion flame near said heated crucible;
   (d) a source of carrier gas;
   (e) conduit means for conducting said carrier gas past said heated crucible and for carrying the vapor of said sample material into said flame;
   (f) an optical detector disposed near said flame for detecting the optical emission from said flame; and
   (g) an optical filter disposed between said flame and said detector, said filter selected to pass wavelength bands characteristic of said sample material.

2. The system of claim 1 wherein said heated crucible comprises a tungsten wound graphite crucible.

3. The system of claim 1 wherein said carrier gas is selected from the group consisting of argon, helium and nitrogen.

4. The system of claim 3 further comprising a source of reactive gas and conduit means for carrying said reactive gas past said heating crucible for reaction with said vapor to produce a reaction product for transport into said flame for analysis.

5. The system of claim 4 wherein said reactive gas is air or oxygen.

6. The system of claim 1 wherein said flame is maintained at a temperature in the range of about 1000° to 1100° C.

7. The system of claim 1 wherein said detector comprises a photomultiplier tube, an avalanche diode detector, a photodiode detector, or a diode array detector.

8. The system of claim 1 wherein said filter is structured to pass 380 nm for the detection of sulfur, or 530 nm for the detection of phosphorus, or 520 nm for the detection of nitrogen containing species, or 360 nm for the detection of chlorine containing species, or 370 nm for the detection of bromine containing species, or 410 nm for the detection of iodine containing species.

9. The system of claim 1 further comprising data collection and storage means operatively connected to said detector and said means for measuring the temperature of said heated crucible.

10. A temperature resolved molecular emission spectrometer system, comprising:
    (a) a controllably heated crucible for vaporizing a sample material for analysis;
    (b) means for measuring the temperature of said heated crucible;
    (c) means for supporting a combustion flame near said heated crucible;
    (d) a source of carrier gas and a source of reactive gas;
    (e) conduit means for conducting said carrier gas and said reactive gas past said heated crucible, for reaction of said reactive gas with the vapor of said sample material to produce a reaction product for transport into said flame for analysis;
    (f) an optical detector disposed near said flame for detecting the optical emission from said flame; and
    (g) an optical filter disposed between said flame and said detector, said filter selected to pass wavelength bands characteristic of said sample material.

11. The system of claim 10 wherein said heated crucible comprises a tungsten wound graphite crucible.

12. The system of claim 10 wherein said carrier gas is selected from the group consisting of argon, helium and nitrogen.

13. The system of claim 10 wherein said reactive gas is air or oxygen.

14. The system of claim 10 wherein said flame is maintained at a temperature in the range of about 1000° to 1100° C.

15. The system of claim 10 wherein said detector comprises a photomultiplier tube, an avalanche diode detector, a photodiode detector, or a diode array detector.

16. The system of claim 10 wherein said filter is structured to pass 380 nm for the detection of sulfur, or 530 nm for the detection of phosphorus, or 520 nm for the detection of nitrogen containing species, or 360 nm for the detection of chlorine containing species, or 370 nm for the detection of bromine containing species, or 410 nm for the detection of iodine containing species.

17. The system of claim 10 further comprising data collection and storage means operatively connected to said detector and said means for measuring the temperature of said heated crucible.

* * * * *